(12) United States Patent
Rickabaugh

(10) Patent No.: US 10,058,402 B2
(45) Date of Patent: Aug. 28, 2018

(54) COLORED DENTAL FLOSS AND A METHOD FOR USING COLORED DENTAL FLOSS

(71) Applicant: Jeff Rickabaugh, Winston-Salem, NC (US)

(72) Inventor: Jeff Rickabaugh, Winston-Salem, NC (US)

(*) Notice: Subject to any disclaimer, the term of this patent is extended or adjusted under 35 U.S.C. 154(b) by 0 days.

(21) Appl. No.: 15/490,206

(22) Filed: Apr. 18, 2017

(65) Prior Publication Data

US 2017/0296305 A1  Oct. 19, 2017

Related U.S. Application Data

(60) Provisional application No. 62/323,891, filed on Apr. 18, 2016.

(51) Int. Cl.
| | |
|---|---|
| *A61C 7/20* | (2006.01) |
| *A61C 15/04* | (2006.01) |
| *A61C 5/00* | (2017.01) |
| *A61C 7/02* | (2006.01) |
| *A61C 7/12* | (2006.01) |
| *A61C 7/14* | (2006.01) |

(52) U.S. Cl.
CPC ............... *A61C 7/20* (2013.01); *A61C 5/007* (2013.01); *A61C 7/02* (2013.01); *A61C 15/041* (2013.01); *A61C 15/043* (2013.01); *A61C 7/12* (2013.01); *A61C 7/145* (2013.01); *A61C 7/146* (2013.01)

(58) Field of Classification Search
CPC .......... A61C 7/20; A61C 7/21; A61C 15/041; A61C 15/043
See application file for complete search history.

(56) References Cited

U.S. PATENT DOCUMENTS

| | | | | |
|---|---|---|---|---|
| 1,578,189 | A |   | 3/1926 | Charles |
| 3,897,796 | A | * | 8/1975 | Erickson .............. A61C 15/041 132/321 |
| 4,380,432 | A | * | 4/1983 | Orlowski ............. A61K 6/0088 433/180 |
| 4,504,229 | A | * | 3/1985 | Garito .................... A61C 5/007 433/215 |
| 4,922,581 | A | * | 5/1990 | Wilson .................. G02C 3/003 24/300 |

(Continued)

*Primary Examiner* — Nicholas Lucchesi
(74) *Attorney, Agent, or Firm* — Global Intellectual Property Agency, LLC; Daniel Boudwin

(57) ABSTRACT

Colored dental floss and a method for using colored dental floss. The colored dental floss includes an elongated filament having a plurality of segments, wherein each segment is a distinct color. The elongated filament is disposed within an interior volume of a container. The container includes an aperture for the elongated filament to pass therethrough. The method of using colored dental floss includes the steps of preparing a lingual side of a plurality of teeth for application of a bonding agent, applying the bonding agent to the lingual side, threading the elongated filament between a desired number of adjacent teeth in sections such that the elongated filament forms a plurality of loops on the lingual side, placing a wire through the plurality of loops, tensioning the elongated filament, applying the bonding agent to a contact point between the lingual side and the wire, curing the bonding agent, and removing the elongated filament.

6 Claims, 4 Drawing Sheets

(56) References Cited

U.S. PATENT DOCUMENTS

| | | | | |
|---|---|---|---|---|
| 5,039,303 | A * | 8/1991 | Irwin | A61C 7/00 433/215 |
| 5,365,874 | A | 11/1994 | Dorfman | |
| 5,526,831 | A * | 6/1996 | Gilligan | A61C 15/042 132/321 |
| 5,692,530 | A * | 12/1997 | Bible | A61C 15/041 132/321 |
| 6,016,816 | A * | 1/2000 | Ariagno | A61C 15/041 132/321 |
| 7,174,903 | B2 * | 2/2007 | Longoni | A61C 15/041 132/321 |
| 7,854,235 | B2 * | 12/2010 | Blanchard | A61C 15/042 132/321 |
| 8,006,708 | B1 * | 8/2011 | Burr, Jr. | A61C 15/041 132/321 |
| 8,439,049 | B2 * | 5/2013 | Lavrova | A61C 15/041 132/321 |
| 8,474,237 | B2 | 7/2013 | Tam et al. | |
| 8,522,796 | B2 * | 9/2013 | Ochs | A61C 15/042 132/239 |
| 8,662,092 | B2 | 3/2014 | Kalbfeld et al. | |
| 2004/0048231 | A1 * | 3/2004 | Perlin | G09B 19/0084 434/263 |
| 2012/0028221 | A1 * | 2/2012 | Williams | A61C 5/007 433/215 |
| 2014/0302448 | A1 * | 10/2014 | Cassalia | A61C 7/28 433/9 |

* cited by examiner

COLORED DENTAL FLOSS AND A METHOD FOR USING COLORED DENTAL FLOSS

CROSS REFERENCE TO RELATED APPLICATIONS

This application claims the benefit of U.S. Provisional Application No. 62/323,891 filed on Apr. 18, 2016. The above identified patent application is herein incorporated by reference in its entirety to provide continuity of disclosure.

BACKGROUND OF THE INVENTION

The present invention relates to dental floss and a method for using dental floss. More specifically, the present invention provides colored dental floss and a method for using colored dental floss to assist in mounting orthodontic wire to teeth.

Many dentists use floss to assist in the installation of dental and orthodontic appliances, such as braces and fixed wire retainers. Wires are pulled against the surface of the tooth with the floss to ensure proper contact with a bonding agent such as cement or other adhesives. However, it can be difficult to determine which tooth the floss is beside when using typical white dental floss, which can lead to frustrating or inefficient installation of the dental appliances. Furthermore, many children are difficult to motivate to floss their teeth, especially with plain white dental floss, which can lead to dental issues such as tooth decay and gum disease in the future. Therefore, a multi-colored dental floss system is provided.

In light of the devices disclosed in the known art, it is submitted that the present invention substantially diverges in design elements from the known art and consequently it is clear that there is a need in the art for an improvement to existing dental floss and methods of using dental floss. In this regard, the instant invention substantially fulfills these needs.

SUMMARY OF THE INVENTION

In view of the foregoing disadvantages inherent in the known types of dental floss and methods for using dental floss now present in the prior art, the present invention provides colored dental floss wherein the same can be utilized for providing convenience for the user when bonding orthodontic wire to teeth.

The present system comprises an elongated filament having a plurality of segments, wherein each segment comprises a distinct color. The elongated filament is disposed within a container having an aperture adapted to fit the elongated filament therethrough. In some embodiments, the container further comprises a spool disposed therein, wherein the elongated filament is adapted to wrap therearound. In other embodiments, the container comprises various shapes, including that of a cartoon character.

The present method comprises the steps of preparing a lingual side of a plurality of teeth for the application of a bonding agent applying the bonding agent to the lingual side. The elongated filament having a plurality of segments, wherein each segment comprises a distinct color, is then threaded between the desired number of adjacent teeth such that the elongated filament forms a plurality of loops on the lingual side. A wire is then placed through the plurality of loops and the elongated filament is then tensioned to tighten the plurality of loops and secure the wire to the lingual side. A bonding agent is then applied to the contact point between the lingual side and the wire, and the bonding agent is cured to secure the wire to the lingual side. The elongated filament is then removed from between the plurality of teeth. In some embodiments, a single segment is threaded between the adjacent teeth such that the elongated filament between each pair of adjacent teeth comprises a single color. In other embodiments, the method further comprises identifying the desired segment to tension. In yet other embodiments, the desired segment to tension is identified based on the color of the segment. In another embodiment, the step of preparing the plurality of teeth for the application of the bonding agent comprises etching the lingual side. In some embodiments, the step of preparing the plurality of teeth for the application of the bonding agent comprises rinsing and drying the lingual side.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
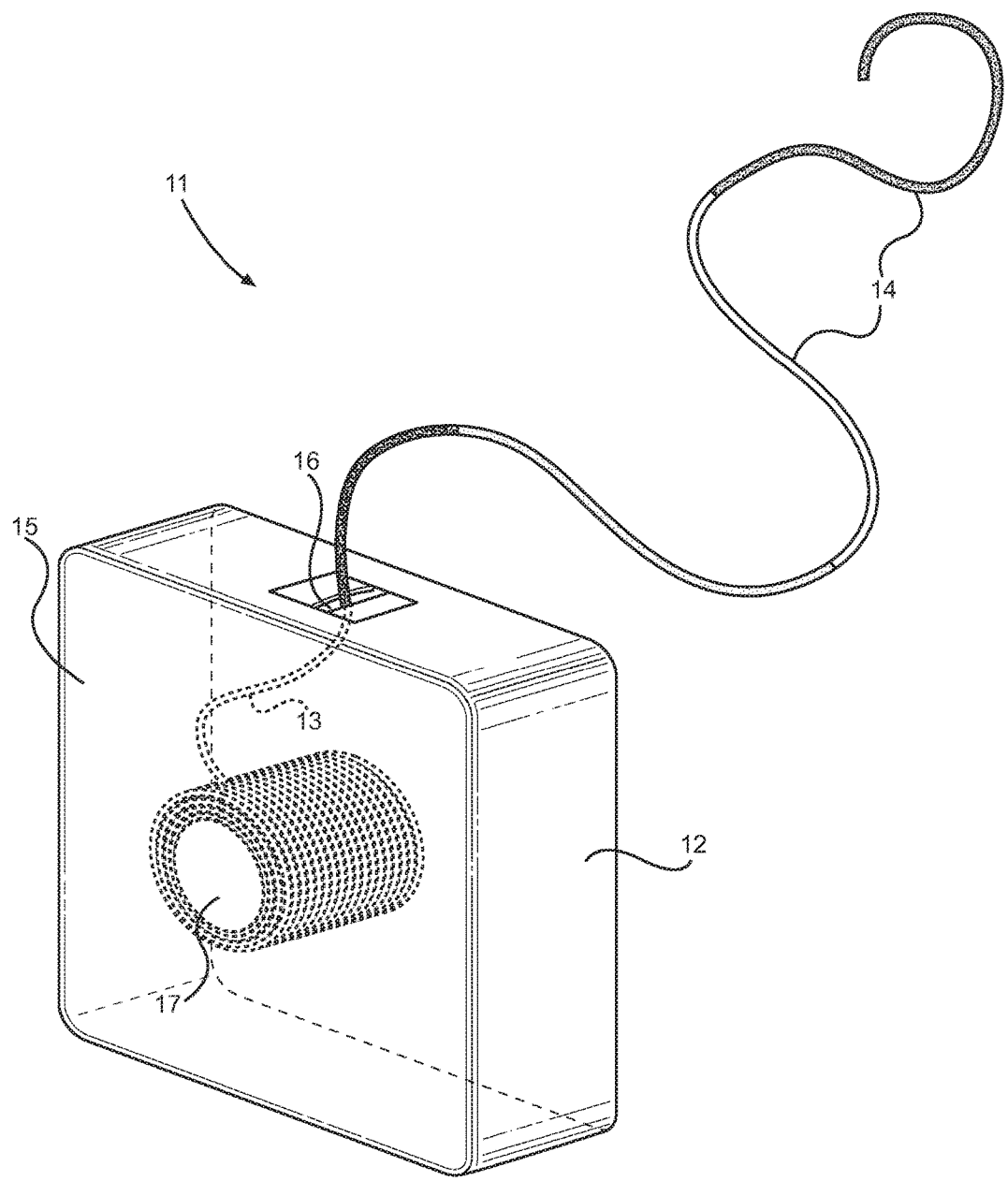
FIG. 1 shows a perspective view of an embodiment of the colored dental floss.

Reference is made herein to the attached drawings. Like reference numerals are used throughout the drawings to depict like or similar elements of the colored dental floss. The figures are intended for representative purposes only and should not be considered to be limiting in any respect.

Figure 2:
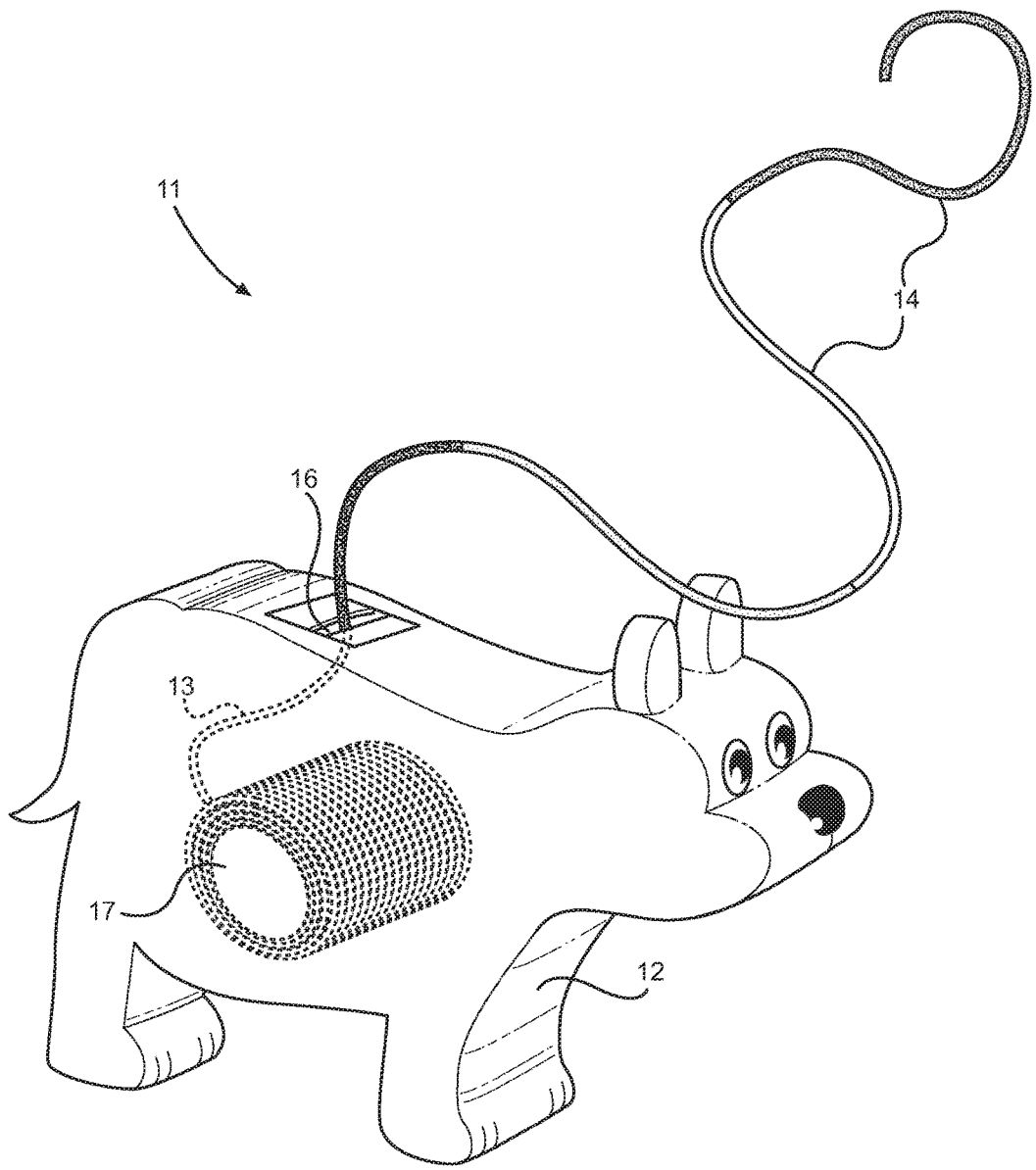
FIG. 2 shows a perspective view of an alternate embodiment of the colored dental floss.

Referring now to FIGS. 1 and 2, there is shown a perspective view of an embodiment of the colored dental floss, and a perspective view of an alternate embodiment of the colored dental floss, respectively. The colored dental floss 11 comprises a container 12 having an interior volume 15. An elongated filament 13 is disposed within the interior volume 15. The elongated filament 13 comprises a plurality of segments 14, wherein each individual segment comprises a distinct color. The various colors provide the user a more engaging flossing experience than that provided by simple white floss. The plurality of segments 14 are spaced at a set length, such that a new color begins at the end of that set length. In some embodiments, the set length is 12 inches. In other embodiments, the set length can vary between segments, such that each individual segment can comprise a different length than another segment. In some embodiments, the elongated filament 13 comprises a wax coating to provide smooth interaction with the user's teeth. In other embodiments, the elongated filament 13 includes a flavoring to provide the user with a pleasant taste while flossing.

In the illustrated embodiment of FIG. 1, the container 12 comprises an aperture 16, wherein the aperture 16 is configured to allow the elongated filament 13 to pass therethrough. In some embodiments, the edge of the aperture 16 is sharpened to allow a user to sever the elongated filament 13 at a desired length. In other embodiments, the container 12 further comprises a spool 17 disposed within the interior volume 15. The spool 17 is configured to feed the elongated filament 13 wrapped therearound. In the illustrated embodiment of FIG. 2, the container 12 can shaped to replicate various popular figures or desired shapes, including but not limited to, sporting equipment, popular characters in sports or entertainment, cartoon characters, beach balls, balloons, geometric shapes, and the like. The various different appearances of the container 12 serve to make the flossing experience more engaging for the user.

Figure 3:
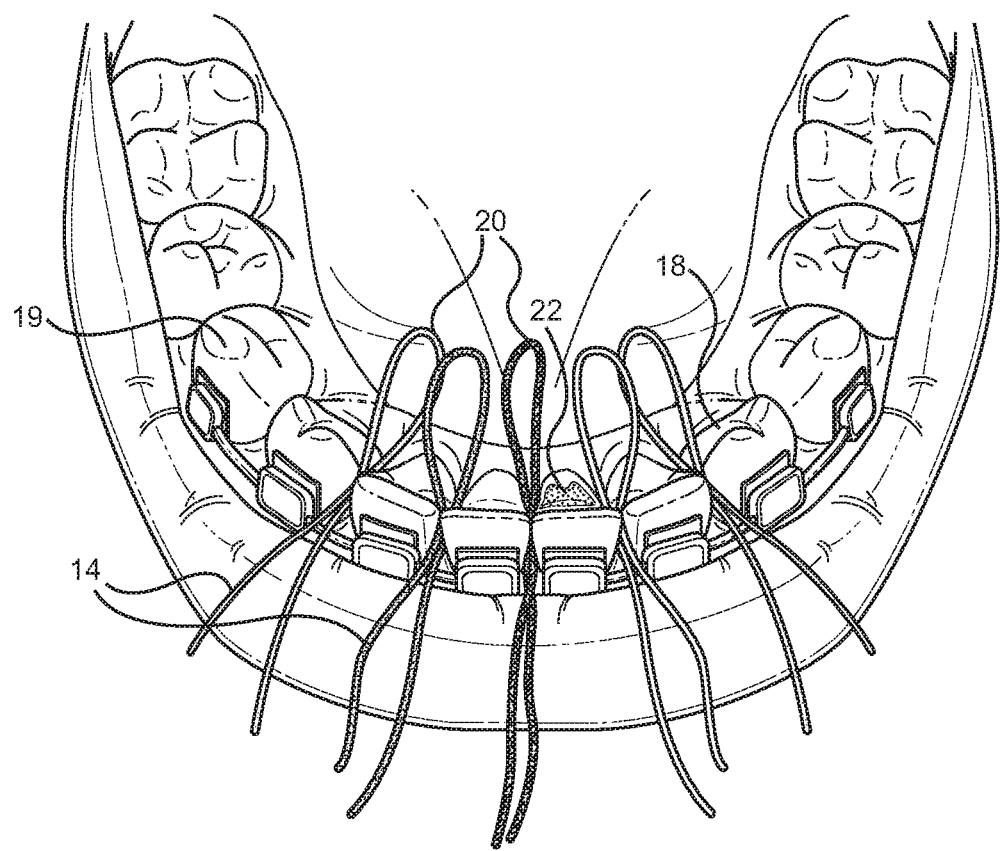
FIG. 3 shows a perspective view of an embodiment of the colored dental floss in use.
Figure 4:
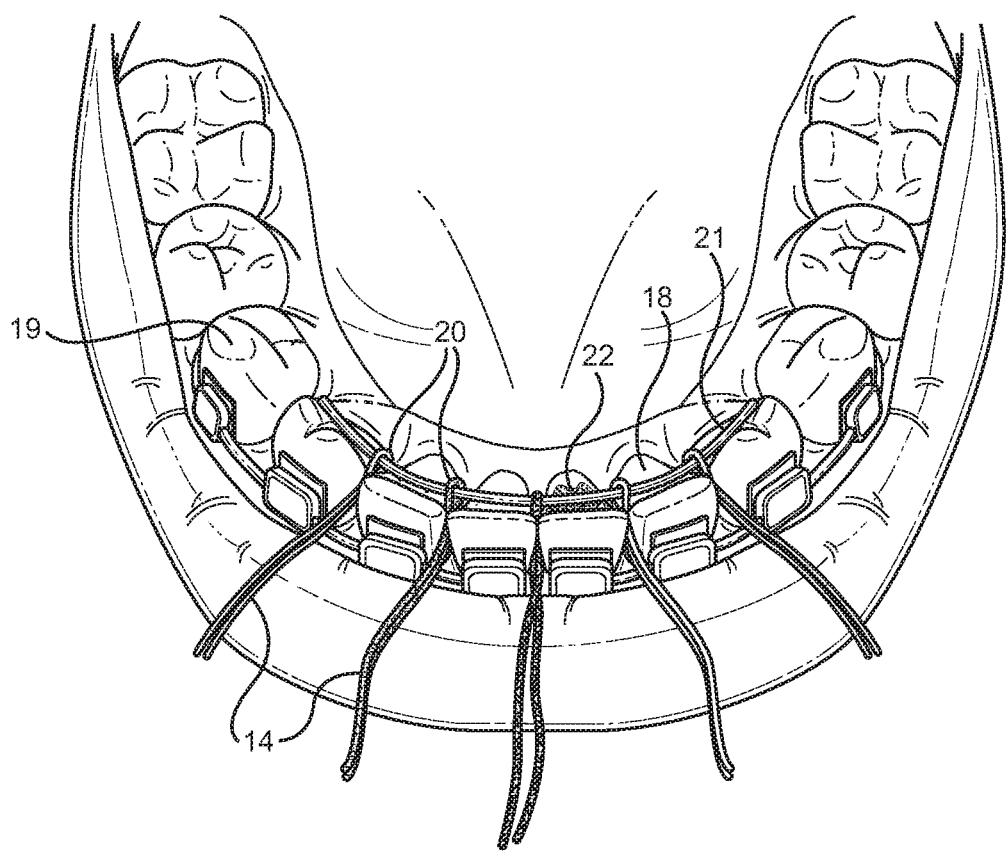
FIG. 4 shows a perspective view of an embodiment of the colored dental floss being tensioned.

Referring now to FIGS. 3 and 4, there are shown a perspective view of an embodiment of the colored dental floss in use and a perspective view of an embodiment of the colored dental floss being tensioned, respectively. A method of using colored dental floss 11 comprises the steps of preparing a lingual side 18 of a plurality of teeth 19 for the application of a bonding agent 22. The plurality of teeth 19 can be prepared to receive the bonding agent 22 through a variety of methods, including but not limited to microetching, acid etching, rinsing, and drying the lingual side 18. The bonding agent 22 is then applied to the lingual side 18 of the plurality of teeth 19.

An elongated filament 13 having a plurality of segments 14, wherein each individual segment comprises a distinct color is then threaded between adjacent pairs of the plurality of teeth 19 such that a plurality of loops 20 are formed on the lingual side 18, as shown in FIG. 3. In the illustrated embodiment, a single segment is threaded between adjacent pairs of the plurality of teeth 19 such that the elongated filament 13 between each pair of teeth comprises a single color. In this way, each pair of adjacent teeth is identified by a single color. This allows the user to differentiate between each pair of adjacent teeth at a glance, to allow a user to identify the correct segment to tension.

A wire 21 is placed through each of the plurality of loops 20, as shown in FIG. 4. The elongated filament 13 is then tensioned to tighten the plurality of loops 20 around the wire 21 to contact the wire 21 with the lingual side 18. In some embodiments, the plurality of segments 14 are tensioned in a desired order so as to provide uniform bonding between the wire 21 and the lingual side 18 of the plurality of teeth 19. A bonding agent 22 is then reapplied to the contact point of the wire 21 and the lingual side 18. The bonding agent 22 is then cured to secure the wire 21 to the lingual side 18. The elongated filament 13 is then removed from between the plurality of teeth 19.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of using colored dental floss, comprising:
preparing a lingual side of a plurality of teeth for the application of a bonding agent;
applying the bonding agent to the lingual side;
threading an elongated filament having a plurality of segments, wherein each segment comprises a distinct color, between the desired number of adjacent teeth such that the elongated filament forms a plurality of loops on the lingual side;
placing a wire through the plurality of loops;
tensioning the elongated filament to tighten the plurality of loops and contact the wire to the lingual side;
applying the bonding agent to a contact point between the lingual side and the wire;
curing the bonding agent to secure the wire to the lingual side;
removing the elongated filament from between the plurality of teeth.

2. The method of using colored dental floss of claim 1, wherein a single segment of the elongated filament is threaded between adjacent teeth, such that the elongated filament between each pair of adjacent teeth comprises a single color.

3. The method of using colored dental floss of claim 2, further comprising identifying a desired segment to tension to provide uniform bonding of the wire across the lingual side.

4. The method of using colored dental floss of claim 3, wherein the desired segment to tension is identified by a distinct color.

5. The method of using colored dental floss of claim 1, wherein preparing the lingual side for a bonding agent comprises etching the lingual side.

6. The method of using colored dental floss of claim 5, further comprising rinsing and drying the lingual side after an etching process.

* * * * *